(12) United States Patent
Byrne

(10) Patent No.: US 6,852,098 B2
(45) Date of Patent: Feb. 8, 2005

(54) FEMALE CATHETER HAVING DISTAL RECESSED APERTURES

(75) Inventor: Phillip Owen Byrne, Newcastle-Upon-Tyne (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 10/296,165

(22) PCT Filed: May 31, 2001

(86) PCT No.: PCT/GB01/02416

§ 371 (c)(1),
(2), (4) Date: Nov. 22, 2002

(87) PCT Pub. No.: WO01/93935

PCT Pub. Date: Dec. 13, 2001

(65) Prior Publication Data

US 2003/0135200 A1 Jul. 17, 2003

(30) Foreign Application Priority Data

Jun. 2, 2000 (GB) .............................. 0013514

(51) Int. Cl.[7] .......................... A61M 31/00; A61F 5/44
(52) U.S. Cl. ..................... 604/279; 604/329
(58) Field of Search ................. 604/328–331, 604/274, 275, 279, 544, 264, 276

(56) References Cited

U.S. PATENT DOCUMENTS

| | | | | |
|---|---|---|---|---|
| 2,043,630 A | * | 6/1936 | Raiche | 264/264 |
| 3,228,396 A | * | 1/1966 | Potts | 604/212 |
| 3,945,385 A | * | 3/1976 | Sackner | 604/119 |
| 4,057,060 A | * | 11/1977 | Roth | 604/200 |
| 4,894,053 A | * | 1/1990 | Reddick | 604/85 |
| 5,271,735 A | * | 12/1993 | Greenfeld et al. | 604/266 |
| 5,295,983 A | * | 3/1994 | Kubo | 604/329 |
| 5,653,700 A | * | 8/1997 | Byrne et al. | 604/329 |
| 5,693,001 A | * | 12/1997 | Salama | 600/29 |
| 5,695,481 A | * | 12/1997 | Heinzelman et al. | 604/279 |
| 6,342,049 B1 | * | 1/2002 | Nichols | 604/329 |
| 2001/0034503 A1 | * | 10/2001 | Mehier | 604/158 |
| 2003/0171722 A1 | * | 9/2003 | Paques et al. | 604/264 |

FOREIGN PATENT DOCUMENTS

| | | | | |
|---|---|---|---|---|
| EP | 0 699 086 B1 | * | 2/1997 | A61M/25/01 |
| EP | 0 873 760 A1 | * | 10/1998 | A61M/25/00 |
| FR | 2 390 967 | * | 12/1978 | A61M/25/00 |

\* cited by examiner

*Primary Examiner*—Larry I. Schwartz
*Assistant Examiner*—Michael G Bogart
(74) *Attorney, Agent, or Firm*—Nixon & Vanderhye

(57) ABSTRACT

A catheter or similar device, particularly a female transient urinary catheter (1), comprises a rigid polypropylene tube having a saw tooth formation (4) providing a flexible region which separates a handle portion (2) from an insertion portion (3). In the insertion portion are formed apertures (6, 9) in the distal tip of the catheter and in the side of the catheter (1) towards the distal end. The tip aperture (6) has a rolled over edge (7) and the side apertures (9) are formed in recesses (8) in the external profile of the catheter. A scaling portion (10) comprises a sinusoidal undulation in the catheter wall which effects an improved seal between the catheter and the wall of the urethra.

10 Claims, 5 Drawing Sheets

FEMALE CATHETER HAVING DISTAL RECESSED APERTURES

This invention relates to catheters and similar devices for insertion into and sealing within vessels in the human or animal body and for insertion into incisions in the human or animal body, eg. for drainage. The invention relates in particular to a device for female transient urinary catheterisation but is not limited to such a device.

Deviation from normal bladder function in a patient can involve problems of urinary retention, whereby the bladder is unable to evacuate urine. This dysfunction can result from a number of different causes, such as congenital defects in the nerve connections to the brain, nerve injuries resulting from trauma to the spinal cord, extensive abdominal surgical operations, infection and various diseases. If the sphincter muscle is too tight or the bladder muscles are too lax the patient may be able to urinate but may be unable to completely empty the bladder during urination.

Patients with urinary retention require catheterisation to enable the bladder to be satisfactorily emptied. In some cases a urine collection bag and an indwelling urethral catheter are used, the catheter forming a passageway from the bladder to the externally-carried collection bag which can regularly be emptied. This arrangement, however, is cumbersome and moreover leaves the patient at increased risk of infection, bacteria being able to grow and track along the catheter from the collection bag or around the catheter along the urethra.

The alternative and more acceptable solution is the insertion of a transient urethral catheter to allow the patient to void in the bathroom when appropriate or on a predetermined time schedule, such as every three to four hours. For women, this intermittent self-catheterisation can be very difficult to carry out. Presently available devices can be difficult to grip and manipulate, being only a thin, flexible plastic tube with a special slippery surface to aid insertion.

Patent Application FR 2 555 903 describes an intermittent catheterisation device comprising a handle and a catheter tube, the handle being used to facilitate the introduction of the catheter tube into the urethra. Once the catheter tube is engaged with the handle their relative positions are fixed except for the limited flexibility permitted by the slight degree of pliancy of the catheter.

European Patent Application EP-A-0699086 describes a catheter which addresses these issues by having a handle portion jointed to a rigid portion for insertion, the two being connected by a flexible joint. The handle portion facilitates grasping of the catheter by a user and the flexible joint allows the insertion portion to be oriented suitably with respect to the handle, depending on the user's anatomy, position or her preferences for how the catheter is handled.

The devices described in EP-A-0699086, whilst being a significant improvement over what had gone before, suffer from a number of disadvantages. The devices described are either fully disposable or have a separate handle and insertion portion, the insertion portion being disposable. In the former case, the devices are more complex and expensive than desirable for a disposable item. In the latter case, the need for the user to carry a separate handle and to fit a new insertion element into the handle for each use is an undesirable complication.

One of the inventors named on the above patent application has realised that a rigid, thin walled tube with a corrugated region for flexing may be used on its own as a catheter with integral handle, the proximal end of the device forming the handle. There is in this case no need for the tube to have any formations on its surface for locking it into place in a separate handle member, although other types of formation may be useful for other purposes as discussed below.

A catheter of this type may be made from a conventional polypropylene drinking straw having a corrugated flexing portion, by sealing one end of the straw (the longer of the sections on each side of the corrugated flexible portion) and punching one or more holes in the wall of the straw near the closed end. A catheter of this type has been tested and found to be very simple to use and effective. It is also very cheap to manufacture. The principal advantages are:

rigidity facilitating insertion flexible portion allows the "handle" region to be oriented as desired, to facilitate insertion thin walls provide for a large lumen for a given external diameter, leading to fast flow rates compared to conventional catheters cheapness of manufacture disposable easy to sterilise using a γ-ray technique.

It will be appreciated that all of the above advantages, apart from the provision of an orientable handle, are available from a rigid thin walled tube without a flexible portion.

A number of improvements to the basic design are also possible. The first of these is to form the holes in the catheter in a recessed region, the sides of the recess ideally having a smooth, rounded and gently sloping shape. This is to avoid the edges of the holes snagging on the interior wall of the urethra when the catheter is inserted and removed. These recesses may be formed by a specially designed punch. The recessed region may take any form and may have one or more apertures in it. Preferably, however, the recessed region extends only around the immediate vicinity of a respective aperture, preferably occupying no more than ten times the surface area of catheter wall taken up by the aperture itself, more preferably no more than five times, still more preferably no more than three times.

A further improvement concerns the sealing of the catheter in the urethra. It has been found that an improved seal is created by a slight bulge in the catheter wall, normally extending around the entire circumference of the catheter. The seal is further improved if the catheter wall is recessed, preferably around its whole circumference, the recessed region preferably being adjacent the bulge. The recess and bulge need not be very extensive in the axial direction of the catheter; for example each may be from 1 to 20 mm in length, preferably 3 to 10 mm. The cross section of each may be roughly circular, or together they may form a gentle sinusoidal undulation in the surface of the catheter. Improving the seal in the urethra helps to avoid urine passing between the catheter and the urethra wall. The effect of the bulge/depression is not entirely understood, but appears to be related to the urethra being tightened around the bulge, and collapsing into the depression. This occurs because the urethra is not a simple conduit with a substantially constant cross section lumen, but is more in the nature of a long smooth muscular tube which opens to allow the passage of urine and closes to prevent the passage of urine, in conjunction with a sphincter.

A further modification/improvement consists in forming a rolled over opening in the end of the catheter. This shape allows insertion to be as easy or almost as easy as when the end is closed-off in a smooth, rounded shape. The same effect can be achieved by manufacturing the catheter with a thickened periphery to the distal hole or by incorporating a bead into the periphery, so that no sharp edge is presented.

It is found that users are more aware of the location of the end of the catheter as a result of the presence or absence or rate of flow or urine from the catheter, when there is an aperture in the distal tip of the catheter. This may have something to do with the catheter deforming the urethra and sphincter somewhat in shear as it is moved inwards and outwards; an end hole will be less susceptible to being occluded by tissue from the wall of the sphincter/urethra bulging into the bladder because of the catheter being inserted and carrying urethra wall tissue with it. An advantage, therefore, of the end hole is that it provides easier control for the user.

The particular advantage of the increased control provided by having a hole in the end of the catheter is that it allows the user easily to ensure that the bladder is completely empty. Leaving a residual volume of urine in the bladder tends to lead to bladder and even kidney infections. In order to provide optimum flow, it is preferred that a catheter with an end aperture also has one or more apertures in the side wall.

In the course of developing the catheter device, the inventor has conceived other applications for a catheter or similar device having one or more of the novel features outlined herein. In many surgical procedures on the human or animal body it is required to insert a catheter or similar device into a vessel of the body, for example a blood vessel, bile duct, fallopian tube or similar. The insertion of such catheters or similar devices can be difficult because of the flexible nature of the device, in the same way that insertion of a flexible urinary catheter can be difficult. There can be similar problems with sealing the catheter against the internal wall of the vessel, and with a conventional thick walled catheter occluding flow through the vessel more than would be desirable. A flexible region on an otherwise relatively rigid catheter may serve either or both of two purposes: (1) facilitating manipulation of the catheter by the surgeon by providing a portion of the catheter which can be arranged to a convenient angle for gripping, and (2) allowing two ends of a vessel to be joined whilst allowing the two joined ends to orient naturally by virtue of a flexible region in the catheter connecting the two vessel ends.

Another application where a relatively rigid, thin-walled tube has significant advantages over a conventional flexible, thick walled catheter is in the draining of wounds, especially post operative draining of surgical sites. Similarly, the invention may be useful as a chest drain.

For these applications, the rigidity of the tube allows for easy insertion and the relatively large lumen for a given outer diameter allows for more efficient drainage. A particular issue with drains, especially chest drains, is that of fastening the tube so that it is not pulled out of the body accidentally. With flexible tubing this is done with sutures and tends to leave the loop of tubing which can snag easily; the procedure is also quite intricate. A rigid tube with a flexible portion allows the tube to be inserted into the body up to the flexible portion and then folded back against the body and eg. taped into place. This is impossible with a conventional tube because bending the tube in this way would cause it to kink and thus restrict or occlude the lumen. For these applications, a tube with a closed distal end, recessed side apertures and a flexible region is preferred.

For drainage, it is envisaged that tubes between 2 mm in diameter for a child and up to 10 mm diameter for an adult human would be used. For a chest drain, the range might be 2 mm to 6 mm. A larger size range would be appropriate for blood vessels and other vessels: 1 mm up to 25 mm for large vessels, say, in a large animal.

Thus according to a first aspect of the invention, a catheter for insertion into a vessel in a human or animal body or for use on a medical drain tube, is provided, which is rigid along substantially all its length, and preferably has one or more of the following additional features:

1. it is thin walled, preferably having walls from $1\mu$ to $300\mu$ thick, more preferably $2\mu$ to $100\mu$, more preferably $5\mu$ to $50\mu$ and still more preferably $10\mu$ to $30\mu$;
2. it is made from polypropylene;
3. it has a sealing region comprising an outwardly extending bulge and/or depression or a gently undulating portion. The properties of the sealing region are preferably as outlined in other parts of the application;
4. it has, at one or both ends, either or both of: (1) an axially facing aperture with a rolled over periphery or a rounded bead around the periphery, or (2) apertures in the side wall which may be in recessed areas of the side wall;
5. a flexible region which may comprise a "crinkle" consisting of a saw tooth formation in the wall of the catheter.

According to a second aspect of the invention, a female urinary catheter is provided having a distal portion for insertion into the urethra, the catheter:

(a) being of substantially rigid construction;
(b) having at least one aperture in its distal portion, the said aperture being located in a recessed region of the catheter wall.

As explained above, a rigid or substantially or relatively rigid design allows easy insertion. A difficulty with rigid materials is that any aperture formed in the wall of the catheter creates an edge which is relatively unyielding and which has the potential to snag on the wall of the urethra on insertion or removal of the catheter. Accordingly, a recessed region may be provided around the or each aperture. The recessed region preferably has relatively smooth contours, and in particular a smooth rounded profile at the junction with the cylindrical outer profile of the catheter, whereby the outer profile merges into the recessed portion in a continuous curve without substantial discontinuities.

The catheter is preferably of unitary construction, comprising in addition to the said distal portion:

(a) a handle;
(b) a flexible region located between said distal portion and said handle.

This provides for simplicity and economy of manufacture, which allows the catheter to be disposable, yet also provides the useful feature of a handle whose orientation with respect to the insertion portion may be set to any desired angle by the user. In this way, the preferences of individual users in terms of technique for insertion, which is a difficult process for many people, may be accommodated. The flexible region may be provided by a so called "crinkle" or saw tooth formation on the wall of the catheter, as is known in drinking straws, which may be collapsed on itself axially and which allows for bending without buckling of the tube with resulting occlusion of the lumen.

Preferably the catheter further comprises, within the said distal portion, a seal comprising a subtle bulge or a relatively smoothly undulating region of the wall. An issue with urinary catheters in general is the leakage of urine around the outside of the catheter tube, when the tube is in place in the urethra. The present invention provides for this novel way of enhancing the seal.

A preferable location for an aperture is in the tip of the catheter, and this has advantages in terms of controllability for the user and the ease with which complete drainage of the bladder may be achieved, as discussed above. Accordingly, a catheter according to the invention may have, in addition or instead of an aperture in the side wall, an aperture in the distal tip, the wall at the edge of said distal tip aperture being rolled over. The wall being rolled over ensures that no edge is presented which may snag on the urethra wall on introduction of the catheter into the urethra. The same effect may be achieved by causing the wall to be thickened around the aperture, with a smooth edge. Alternatively an annular bead may be incorporated into the catheter tip.

It will be appreciated that many of the features described above are novel in their own right, at least in the field of urinary catheters and other catheter devices. Thus, other aspects of the invention include the following.

A third aspect of the invention provides for a female urinary catheter of unitary, substantially rigid construction comprising:
(a) a distal insertion portion;
(b) a handle;
(c) a flexible region located between the said distal portion and the said handle.

The other features described above, e.g. the recessed region around the apeiture in the side wall, the distal tip aperture, the seal and the thin walled construction, are all possible enhancements of the second aspect of the invention.

As discussed above, it will be appreciated that the seal comprising a bulge and/or depression or gently undulating portion of the wall may be useful on other tubes which it is desired should form a good seal with a conduit in the body, particularly a conduit which has the capability to constrict and dilate. An example of such a vessel might be a human artery which has been surgically divided for the purpose of shunting or diverting blood.

Accordingly a fourth aspect of the invention provides for a catheter or similar synthetic structure for insertion into a conduit of the human or animal body, having a sealing region comprising a gentle bulge and/or depression or a gently undulating portion. If the sealing region comprises an outwardly extending bulge, then the radial extent of the bulge is preferably 3–30% of the nominal outer diameter of the tube, more preferably 5–20%. The undulation is preferably substantially sinusoidal and preferably extends over at least one full period of the sinusoidal function. The peak-to-peak amplitude of the undulation, which preferably extends both above and below the general outline of the tube, is preferably 5–50% of the nominal total tube diameter, more preferably 20–40%. The seal region preferably extends around the entire circumference of the catheter and may extend over 1 to 40 mm, more preferably 6 to 20 mm. In a urinary catheter, the seal may also provide the user with an indication of the insertion depth of the catheter, since it may be felt when it enters the meatus. Preferably the distal end of the sealing region is 10–150 mm from the distal tip, more preferably 20–100 mm, more preferably 30–80 mm, when the said synthetic structure is a female urinary catheter. The catheter may have two sealing regions for sealing in respective ends of, eg., a divided artery. The catheter may have a flexible region to allow each end to align with the natural orientation of the respective end of the artery or other vessel. Two or more distinct sealing regions may also provide an even better seal in, say, a urinary catheter device.

In a fifth aspect, the invention comprises a female urinary catheter, substantially of rigid construction, having an axially facing aperture in its distal tip, the wall of the catheter around the edge of the aperture being rolled over. Preferably, the catheter will have an additional aperture or apertures in the side wall at or near its distal end, and these apertures preferably are formed in recessed regions of the side wall.

In a sixth aspect, the invention comprises a female urinary catheter comprising a unitary extruded tube having a thin wall. Preferably the wall is from $1\mu$ to $200\mu$ thick, more preferably $2\mu$ to $100\mu$, more preferably $5\mu$ to $50\mu$, more preferably $10\mu$ to $30\mu$. The tube is preferably rigid along substantially all its length and is preferably polypropylene. The outer diameter of the tube over the majority of its length (ie. excluding protruding portions such as a seal) may be from 2 mm for children to 7 mm for adults. A normal adult size might be 4–5 mm.

In a seventh aspect of the invention, a drain tube for the human or animal body is provided, the tube being relatively rigid along substantially all its length, but preferably having a flexible region as described herein. Preferably, the tube has a closed end and two or more, preferably five or more, side wall apertures at different longitudinal and different circumferential positions with respect to the tube. The apertures are normally located in a distal insertion region which is from 10 to 50 mm long, preferably 20 to 40 mm long.

In an eighth aspect of the invention, a method of urinary catheterisation is provided, comprising periodically inserting the into the urethra a catheter having the features outlined in any of the paragraphs above.

In a ninth aspect of the invention, a method of draining a wound is provided, comprising inserting into the wound a catheter or tube as described in any of the paragraphs above.

In a tenth aspect of the invention, a method of installing a chest drain is provided, comprising making an incision in the chest wall of a human or animal patient, and inserting into the incision a catheter or tube as described in any of the paragraphs above. Preferably a tube as described above with a flexible region between 10 and 50 mm from the distal tip is used, in which case the method may involve inserting the tube up to the flexible region and then bending the tube at the flexible region so that its proximal end portion lies flat against the outside of the patient's body.

In an eleventh aspect of the invention, a method of re-joining a severed vessel of a human or animal body, eg. a blood vessel, is provided comprising inserting respective ends of a catheter as described in any of the above paragraphs into respective ends of the severed vessel.

In a twelfth aspect of the invention, a method of catheterising a vessel of the human or animal body, eg. a blood vessel, bile duct or fallopian tube, comprises inserting into the vessel a catheter or tube as described in any of the above paragraphs.

BRIEF DESCRIPTION OF THE DRAWINGS

The invention will now be described in more detail with reference to specific embodiments. The description is by way of example only, and is made with reference to the accompanying figures in which.

DETAILED DESCRIPTION OF PREFERRED EMBODIMENTS

Similar parts in the various modifications are referred to using the same reference numerals.

Figure 1:
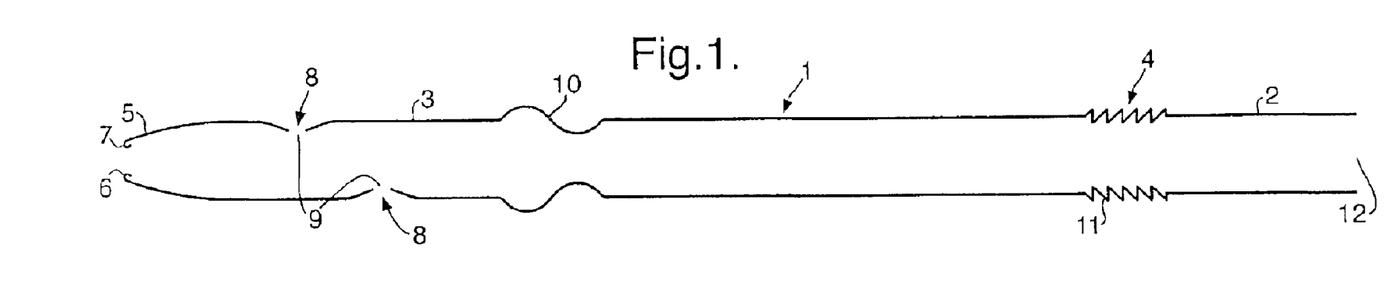
FIG. 1 is a side sectional view of a transient urinary catheter according to the invention.

Referring to FIG. 1, a female transient urinary catheter comprises a circular cross-section tube 1 of 20μ thick polypropylene. The outer diameter, for the majority of its length, is 4.7 mm. The catheter is 209 mm in length and is divided into a handle portion 2 and insertion portion 3, separated by a flexible region 4. Over the majority of its length, the catheter is substantially rigid. The handle portion is 49 mm, the flexing region (in its non-compressed state) 21 mm and the insertion portion 139 mm long. In practice this would be one of a range of sizes of catheter to suit different patients, from 2 mm diameter for child up to 7 mm for a large adult.

Starting from the left hand side in the Figure, the catheter comprises a tip region 5 which is of gently rounded shape, narrowing towards the tip itself (the distal tip). An aperture 6 is formed in the tip, with the wall around the aperture 6 being rolled over to provide a rounded edge 7 to the aperture 6. The diameter of the aperture is approximately 1.9 mm.

Moving towards the right in the Figure, approximately 20 and 30 mm from the distal tip of the catheter, respectively, are recesses 8 in the outer profile of the catheter. The dimensions of the recesses are 8 mm in the axial direction, 3 mm in the transverse direction and 1 mm deep, approximately. The approximate dimensions of the apertures 9 are 5 mm axially and 2 mm transversely. It will be observed that the recesses are formed by curves substantially continuous with the nominal outer profile of the catheter, with any significant discontinuities being avoided.

Continuing along the catheter from left to right, starting approximately 60 mm from the distal tip, is an undulating portion 10 of the wall. The undulation comprises a simple sinusoidal curve in section (rotated about the axis of the catheter to form the undulating surface). The undulation extends for one complete period of the sinusoidal function, with a peak to peak amplitude of 2 mm approximately. The curve extends at its peak approximately 1 mm beyond the nominal outer surface and at its trough approximately 1 mm inside the nominal outer surface.

Further along the catheter, some 149 mm from the distal tip, is a series of six saw tooth formations 11 formed in the catheter wall, extending around the periphery of the catheter. In a modification, which is preferred, 10 or more saw tooth formations are provided. Each formation 11 comprises a sloping portion and a portion substantially orthogonal to the axis of the catheter. As is known from the field of drinking straws, such formations may be collapsed to provide a flexible portion of the tube, but in its extended state the saw tooth region is some 21 mm long. The formations 11 each extend radially approximately 0.5 mm beyond and within the nominal outer surface of the tube respectively.

On the right hand side of the flexible region 4 in the Figure, the tube continues for a further 49 mm to form a handle 2. The catheter has a simple opening 12 at its proximal end.

The catheter is manufactured by extruding a uniform tube of polypropylene, which is then processed to produce a catheter of appropriate length and with the necessary apertures and formations in its wall.

The material is not critical, but biocompatible plastics materials, such as polypropylene, are preferred. It has also been found that polypropylene has the required degree of rigidity and durability, and is also relatively inexpensive. To allow for sterilisation, a type of polypropylene is used which has been formulated to inhibit formation of free radicals or to capture free radicals, during γ-ray sterilisation. This type of polypropylene is well known in the medical devices art.

Continuous extruded polypropylene tubing, in this case 4.7 mm in diameter, is fed to a cutting machine, and the cut lengths of tube are collected in a hopper. From there they are fed to a cold rolling machine which forms the saw tooth and sine wave features; a mandrel, with the appropriate shape machined into its surface, is inserted into the tube, and rollers engaged with the tube to press the shape into the surface of the tube. The plastic memory of the polypropylene means that when the machine is withdrawn, the shape stays in the wall of the tube. The gentle slopes of the sine curve and the saw tooth allow easy withdrawal from the mandrel.

The tube is then fed to a machine for creating the shape of the distal tip. The end of the tube is inserted into a thin walled stainless steel thimble which is heated by r.f. heating coils. At the base of the interior of the thimble is a pointed spigot for creating the aperture 6. As the tube enters the thimble it is heated to a temperature at which the polypropylene becomes thermally malleable, and the rolled over edges form as the tube bears down over the spigot.

In a modified process, there is no spigot in the thimble and the tube is formed into a smooth, rounded closed end. In either case, the thimble is immediately cooled by compressed air or nitrogen gas. The tube is then withdrawn. This whole process takes little more than one second, due to the low thermal intertia of thimble and tube.

The tube is then passed to a high speed punch system which forms both the side apertures 9 and depressions 8. The punch comprises a perpendicular-sided cutting portion mounted on a larger cross section block with a gently curved front face. The hole is formed by the cutting head, whilst the curved face plasticly deforms the region around the aperture to provide the recess 8. This process is essentially a cold one, although the punch operates at such speed that there will be a temperature change, created incidentally, but which may assist in the formation of the recess.

The catheter is supplied with the handle 2 folded against the insertion portion 3 in a sterile package. The entire unit is extremely light and compact and may be produced at minimal cost so that there is no difficulty in treating the item as a disposable. In practice a user may carry several in, say, a handbag without difficulty. The catheter may be supplied with a lubricant applied to the insertion portion, although in practice this has not been found necessary.

When the time comes for the patient to evacuate her bladder, she opens a package and folds out the catheter from the handle such that it projects transversely from the handle in a desired orientation. She then holds the handle and, in a sitting position on a toilet seat, locates the meatus of the urethra, inserting the distal end 4 of the catheter to the correct distance. The correct distance is usually of the order of 60 mm or so in an adult. The length of the adult female urethra is approximately 30–40 mm; the three apertures 6, 9 should be inside the bladder. The bladder will then drain via the apertures 6, 9, the urine passing through the catheter lumen and out through the opening at the proximal end 12 into the toilet bowl. When evacuation is complete the catheter is removed from the urethra and the whole unit is discarded.

When the catheter is in place in the urethra, the undulating seal places the smooth muscular wall of the urethra in greater tension around the protruding part of the seal. The wall of the urethra then closes in around the recessed portion of the seal. It has been found that this localised deformation/stressing of the urethra considerably improves the seal between urethra and catheter, without making it significantly more difficult to insert the catheter. The seal portion may be positioned on the catheter so that the user can be reasonably certain that once the seal is fully inserted into the urethra, all the apertures 6, 9 are open to the interior of the bladder. Since in the majority of patients, the undulation may be felt when it is inserted, this provides a way of indicating or facilitating correct insertion depth.

When the flow of urine stops, the user slowly withdraws the catheter. Often, on starting to withdraw the catheter, it is observed that the urine flow re-starts. The reason for this is that the most proximal of the apertures 9, when the catheter is fully inserted, may be above the surface of a residual volume of urine in the bladder. Withdrawing the catheter slowly allows this urine to be voided fully through the apertures 6, 9. The distal tip aperture 6 has been found particularly helpful in ensuring complete voiding of the bladder. It will be appreciated that, due to the orientation of the tip aperture 6, it will remain unoccluded when being withdrawn through the entrance of the bladder to the urethra, and may even provide a lumen when it is a few millimeters into the urethra.

Figure 5:
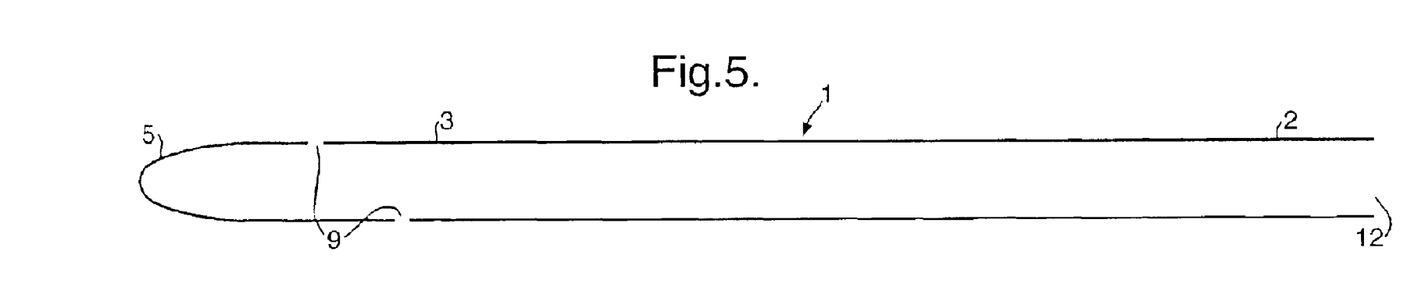
FIG. 5 is a side sectional view of a fourth modification of the catheter of FIG. 1.

Various modifications of the device described above are possible. A device is currently in confidential clinical trials which has a closed rounded distal tip, side apertures without recesses and no undulating seal. Although it requires careful insertion and withdrawal, users have reported very favourably on its ease of insertion and general convenience, and especially its fast flow rate. Accordingly, even a simple thin walled rigid plastics tube with, or even without, a flexing portion and with simple punched side apertures and a rounded closed distal tip appears to represent a considerable improvement over the more normal flexible, thick (0.5 mm) walled catheters which can be difficult to insert and have a smaller lumen for a given external diameter. Such a catheter is shown in FIG. 5.

It is desirable for the potential flow rate through the apertures to be equivalent to that through the length of the catheter, for a given pressure. For this reason, a distal tip aperture alone is not preferred since the diameter of the distal aperture must be less than the lumen. Nevertheless, such a modification would still have the advantages described above in terms of controlling complete emptying of the bladder, and would still probably have a flow rate equivalent to a conventional catheter.

The undulating seal is clinically helpful, but not essential. Particularly because the drain rate is so fast, urine "leakage" is not a serious problem with this catheter even when no undulating seal is used.

The flexing portion 4, providing a handle region 2, is extremely helpful for manipulating the catheter for insertion, but is not essential. One could envisage a catheter which represented a considerable improvement over conventional urinary catheters in terms of flow rate and economy at least, but which does not have a flexing region and is substantially rigid over its entire length.

Figure 2:
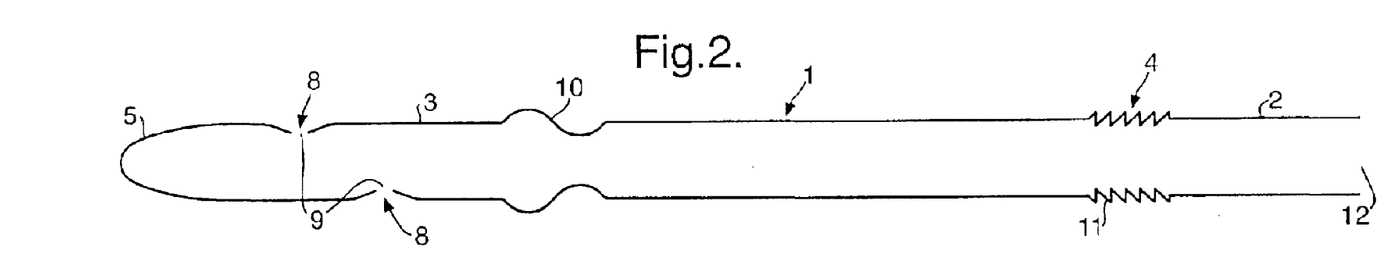
FIG. 2 is a side sectional view of a first modification of the catheter of FIG. 1.
Figure 3:
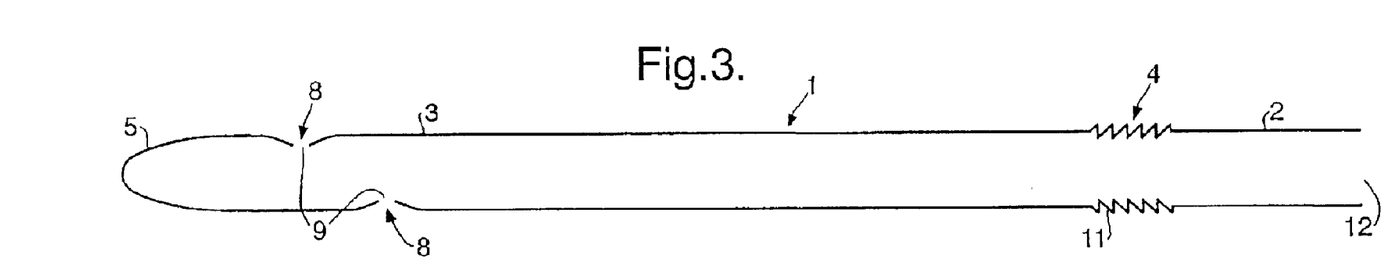
FIG. 3 is a side sectional view of a second modification of the catheter of FIG. 1.
Figure 4:
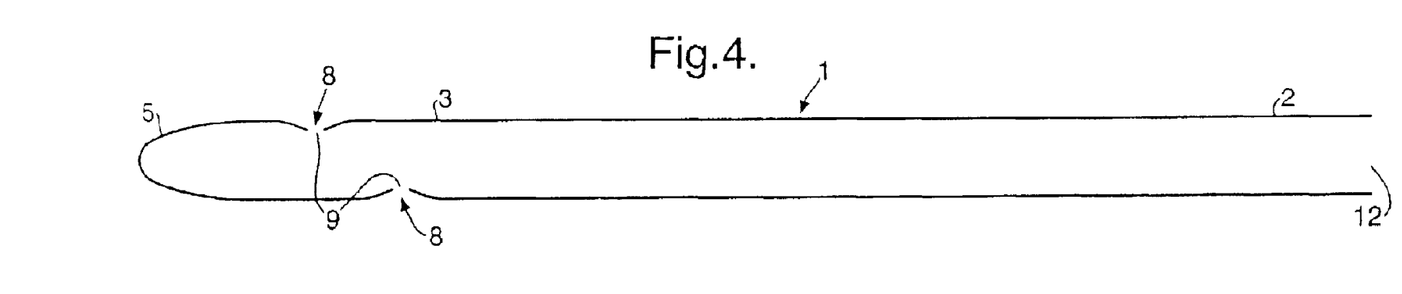
FIG. 4 is a side sectional view of a third modification of the catheter of FIG. 1.
Figure 6:
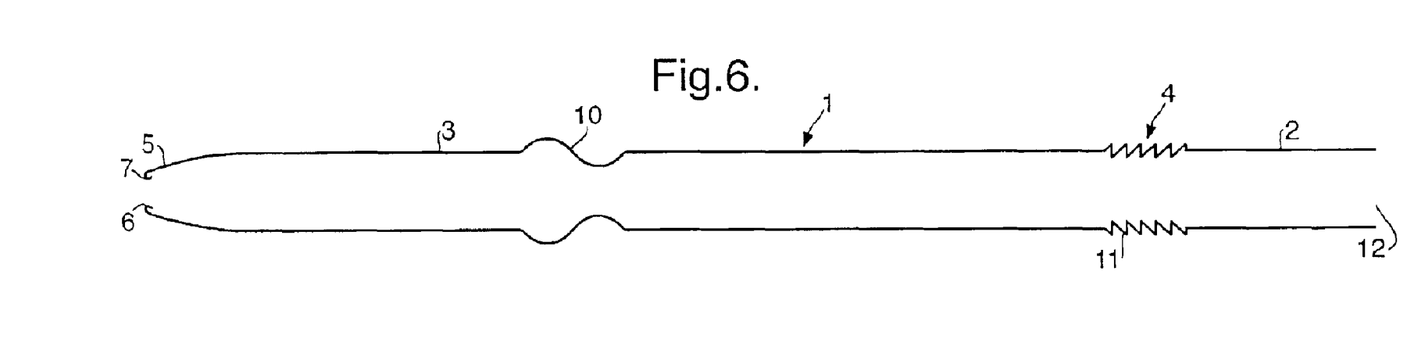
FIG. 6 is a side sectional view of a fifth modification of the catheter of FIG. 1.
Figure 7:
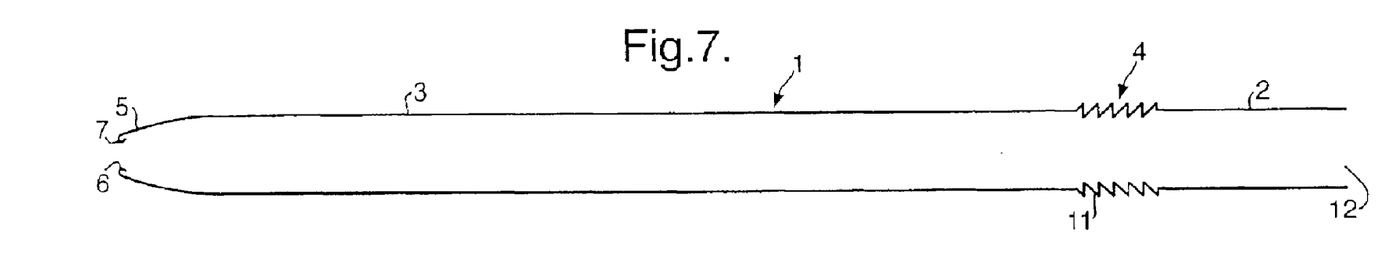
FIG. 7 is a side sectional view of a sixth modification of the catheter of FIG. 1.
Figure 8:
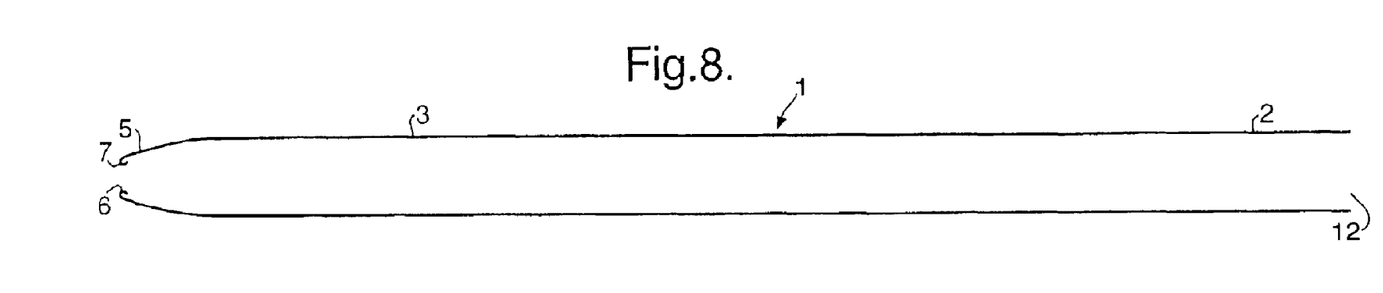
FIG. 8 is a side sectional view of a seventh modification of the catheter of FIG. 1.
Figure 9:
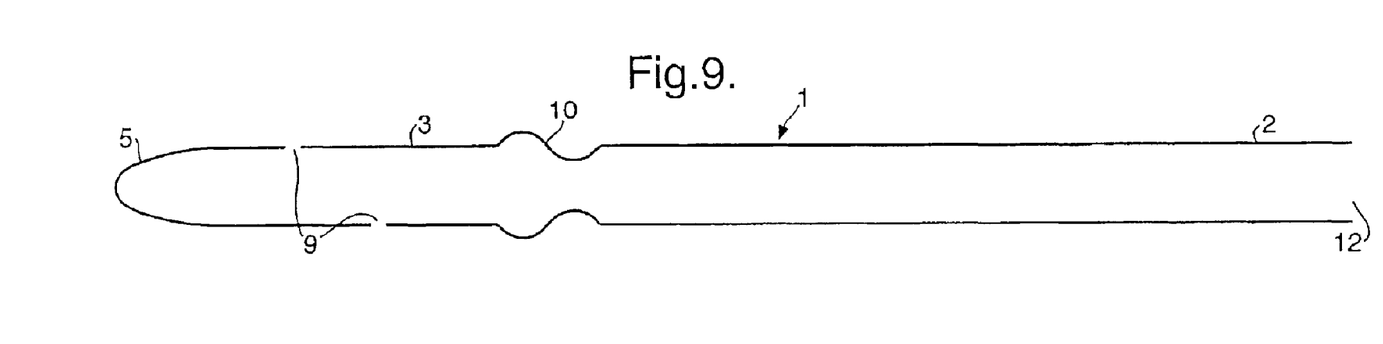
FIG. 9 is a side sectional view of an eighth modification of the catheter of FIG. 1.

FIGS. 2 to 9 show various embodiments of the invention, having different combinations of novel features. FIG. 2, for example, shows a catheter with no distal tip aperture but with recessed side apertures and a flexible region. FIG. 3 shows a catheter with no distal tip aperture and no sealing region, but with recessed side apertures and a flexible portion. FIG. 4 shows an even simpler catheter with no flexible portion. FIG. 5, as discussed above, shows a still more simple catheter, of a type currently in confidential trials. FIGS. 6, 7 and 8 show embodiments with no side wall apertures. FIG. 9 shows a catheter similar to the catheter of FIG. 5, but with a sealing region.

Figure 10:
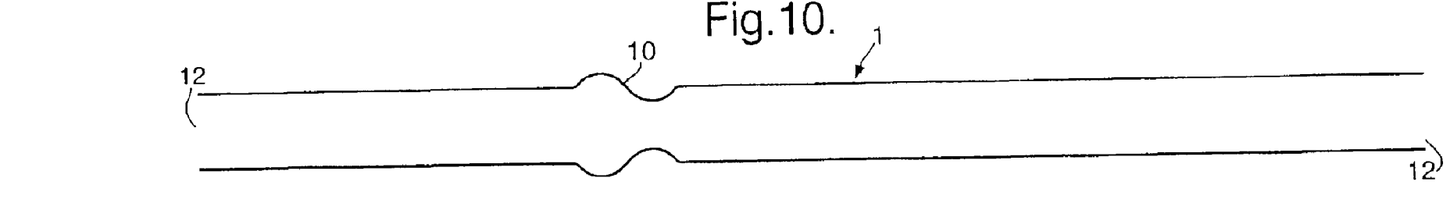
FIG. 10 is a tube for medical or surgical use having a seal region according to the invention.
Figure 11:
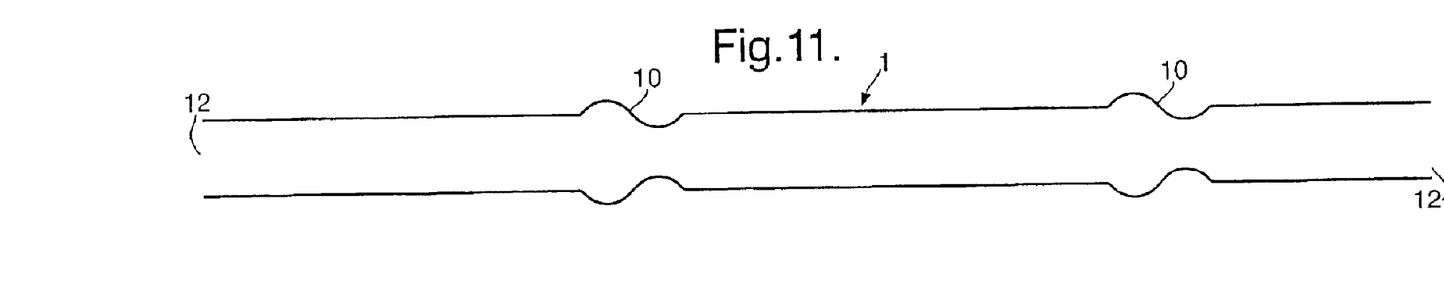
FIG. 11 is a tube similar to that shown in FIG. 10.
Figure 12:
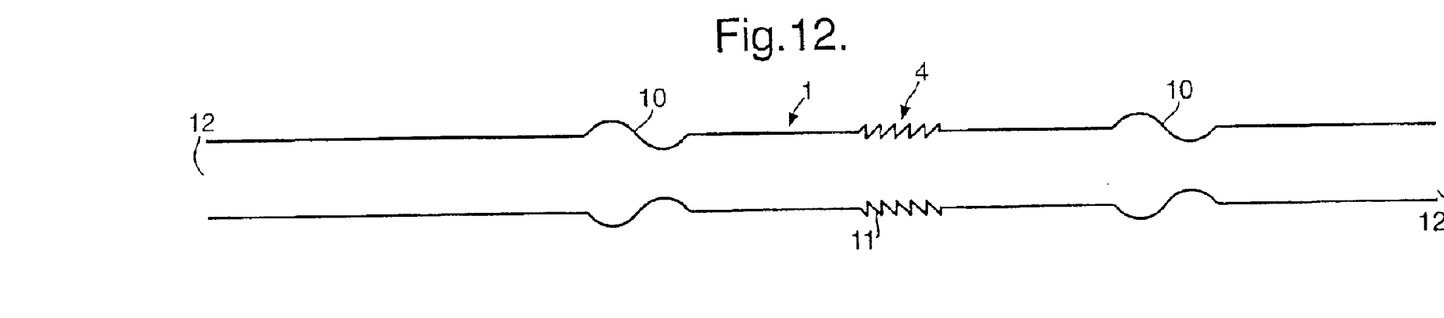
FIG. 12 is a tube similar to that shown in FIG. 11, having two seal regions and a flexible region.

FIG. 10 shows a general purpose medical tube which could be used for example to insert in and seal within some vessel, eg. a blood vessel within the human or animal body. FIG. 11 shows a similar tube with two sealing regions, eg. for using in re-joining the two ends of a severed blood vessel. FIG. 12 shows the same device with a flexible region.

Figure 13:
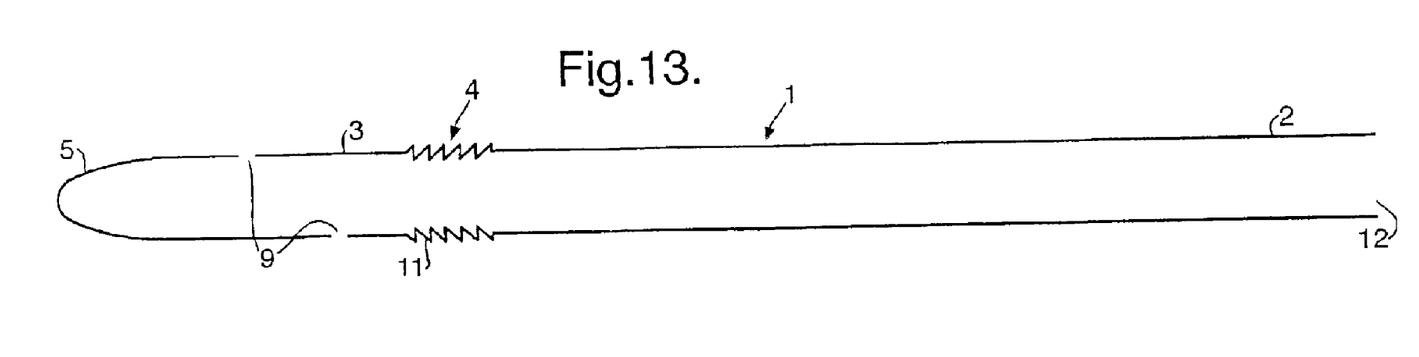
FIG. 13 is a tube with a flexible region near the distal end, suitable for use as a chest drain or wound drain.

FIG. 13 shows an embodiment particularly suitable for use as medical drain (although the other embodiments and modifications could also be used for this purpose). The flexible portion is nearer the distal end, eg. 10–50 mm (in this case 30 mm) from the distal end. This corresponds to the distance to which a chest drain would be inserted in the body, and allows the proximal part of the tube to be folded flat against the body when the tube is in place. The tube may then easily be taped to the skin of the patient to fasten it in place.

What is claimed is:

1. A female urinary catheter having a distal portion for insertion into the urethra, the catheter:
    (a) being substantially of rigid construction;
    (b) having a wall thickness of between $2\mu$ and $100\mu$;
    (c) having at least one aperture in its distal portion, the said aperture being located in a recessed region of an outer surface of the catheter wall.

2. A catheter as claimed in claim 1, in which the said recessed region is formed by an area of wall which is deformed inwardly to provide said recessed region in the outer surface and a corresponding protrusion in an inner surface of the wall.

3. A catheter as claimed in claim 1, being formed from a single piece of tubing and comprising, in addition to said distal portion:
    (a) a handle;
    (b) a flexible region located between said distal portion and said handle.

4. A catheter as claimed in claim 2, being formed from a single piece of tubing and comprising, in addition to said distal portion:
    (a) a handle;
    (b) a flexible region located between said distal portion and said handle.

5. A catheter as claimed in claim 1, further comprising, within the said distal portion, a seal comprising a gentle bulge and, optionally, a depression.

6. A catheter as claimed in claim 1, further comprising, within its distal portion, a seal comprising a relatively smoothly undulating region of the wall.

7. A catheter as claimed in claim 5, wherein an aperture is formed in the distal tip of the catheter, the wall at the edge of said distal tip aperture being rolled over or having a thickened and rounded profile or having a bead incorporated in it.

8. A catheter as claimed in claim 5 having a distal tip at an extreme distal end of the catheter, and wherein said seal has a distal and a proximal end, the distal end of the seal being located between 30 and 80 mm from the distal tip of the catheter, the seal thereby providing a tactile indication to a user upon insertion of the catheter when a correct insertion depth has been reached.

9. A catheter as claimed in claim 3 being formed from a single piece of extruded polypropylene tubing.

10. A catheter as claimed in claim 4 being formed from a single piece of extruded polypropylene tubing.

\* \* \* \* \*